(12) United States Patent
Choi et al.

(10) Patent No.: US 9,801,998 B2
(45) Date of Patent: Oct. 31, 2017

(54) STRUCTURE HAVING NANOANTENNA AND METHOD FOR MANUFACTURING SAME

(75) Inventors: Sung Hoi Choi, Moscow, ID (US);
Jung Rae Park, Andover, MA (US);
Young Keun Kim, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 1128 days.

(21) Appl. No.: 13/982,856

(22) PCT Filed: Jan. 31, 2012

(86) PCT No.: PCT/KR2012/000744
§ 371 (c)(1),
(2), (4) Date: Jul. 31, 2013

(87) PCT Pub. No.: WO2012/105797
PCT Pub. Date: Aug. 9, 2012

(65) Prior Publication Data
US 2013/0317421 A1    Nov. 28, 2013

(30) Foreign Application Priority Data
Jan. 31, 2011    (KR) ...................... 10-2011-10009823

(51) Int. Cl.
*A61K 9/00*    (2006.01)
*A61M 5/172*    (2006.01)
(Continued)

(52) U.S. Cl.
CPC ....... *A61M 5/1723* (2013.01); *A61K 41/0052* (2013.01); *A61M 31/002* (2013.01);
(Continued)

(58) Field of Classification Search
CPC ................................................. A61K 41/0052
See application file for complete search history.

(56) References Cited

U.S. PATENT DOCUMENTS

| | | |
|---|---|---|
| 2006/0276879 A1 | 12/2006 | Lye et al. |
| 2010/0303716 A1 | 12/2010 | Jin et al. |
| 2013/0148194 A1* | 6/2013 | Altug ................... G01N 21/658 359/350 |

FOREIGN PATENT DOCUMENTS

| | | |
|---|---|---|
| KR | 100802139 B1 | 1/2008 |
| KR | 1020090082825 A | 7/2009 |

(Continued)

OTHER PUBLICATIONS

International Search Report; dated Aug. 22, 2012; PCT/KR2012/000744.

*Primary Examiner* — Paul Dickinson
(74) *Attorney, Agent, or Firm* — Ladas & Parry LLP

(57) ABSTRACT

The present invention relates to a structure having a nanoantenna, a method for manufacturing same, a drug delivery body having the same, a thermotherapy complex, a drug therapy device, and a thermotherapy device. The structure of the present invention has a nanoantenna pattern formed on the outer surface of a porous micro-container, thereby enabling wireless control from the outside, and when the structure is used as a drug delivery system and a thermotherapy complex, drug therapy and thermotherapy can be carried out at a desired application region inside a living body at a desired time. Also, the structure of the present invention enables transmission and reception of a wireless signal with an external controller through the nanoantenna, thereby enabling the detection of a signal inside the living body and the transmission of the signal to the external controller, and the discharge of a drug or nanowires according to a response signal transmitted from the external controller.

19 Claims, 6 Drawing Sheets

(51) Int. Cl.
*H01Q 1/22* (2006.01)
*A61M 31/00* (2006.01)
*H01P 11/00* (2006.01)
*H01Q 17/00* (2006.01)
*A61K 41/00* (2006.01)

(52) U.S. Cl.
CPC .............. *H01P 11/003* (2013.01); *H01Q 1/22* (2013.01); *H01Q 17/002* (2013.01); *Y10T 29/49016* (2015.01)

(56) References Cited

FOREIGN PATENT DOCUMENTS

| | | |
|---|---|---|
| KR | 1020090093169 A | 9/2009 |
| KR | 1020090131364 A | 12/2009 |
| KR | 100943993 B1 | 2/2010 |

* cited by examiner

STRUCTURE HAVING NANOANTENNA AND METHOD FOR MANUFACTURING SAME

CROSS-REFERENCE TO RELATED APPLICATION

This application claims priority to and the benefit of Korean Patent Application No. 2011-0009823, filed Jan. 31, 2011, the disclosure of which is incorporated herein by reference in its entirety.

BACKGROUND

1. Field of the Invention

The present invention relates to a structure including a nanoantenna, a method of manufacturing the same, and a drug delivery system, thermotherapy complex, drug therapy device, and thermotherapy device including the same.

2. Discussion of Related Art

Nanoliter-sized chemical delivery systems and devices, such as micelles, vesicles, droplets, and capsules, make it possible to spatially and temporally control a chemical field with a very small volume of reagent. These chemical delivery systems may be used for micro-release of chemical materials, local drug delivery, delivery of biomolecules, thermotherapy, etc.

In the future, various functions are expected to be integrated in a single chemical delivery system. As integrable functions, there is sensing, actuation, telemetry, etc. As one means to achieve these functions, an electric and optic module may be formed on an outer surface of the delivery devices.

At present, it is possible to fabricate a small integrated module using various nanofabrication technologies. The module may act as a sensor, a detector, and a controller. This kind of module has advantages, such as small size, low power consumption, and proper cost consumption. However, there is a problem in that it is risky to apply on a macroscopic scale. However, since a module such as an antenna is easily connected to a wireless signal, this problem may be solved.

SUMMARY OF THE INVENTION

An objective of the present invention is to provide a structure including a nanoantenna, a method of manufacturing the same, and a drug delivery system, thermotherapy complex, and treatment device including the same.

In accordance with an aspect of the present invention, a structure includes a porous micro-container, and a nanoantenna pattern formed on an outer surface of the porous micro-container.

In accordance with another aspect of the present invention, a method of manufacturing a structure includes forming a nanoantenna pattern on an outer surface of a porous micro-container using a focused ion beam system.

In accordance with still another aspect of the present invention, a drug delivery system includes a structure of the present invention, and a pharmaceutically active ingredient impregnated in a porous micro-container of the structure.

In accordance with still another aspect of the present invention, a thermotherapy complex includes a structure of the present invention, and nanowires impregnated in a porous micro-container of the structure.

In accordance with still another aspect of the present invention, a drug therapy device using a drug delivery system includes the drug delivery system of the present invention, a biosensor located on an outer surface of the drug delivery system and configured to detect bioinformation of the inside of a living body, a transmission module configured to receive the bioinformation from the biosensor and wirelessly transmit the bioinformation to an external controller through a nanoantenna pattern formed on the outer surface of the drug delivery system, a receiving module configured to wirelessly receive a drug releasing signal corresponding to the bioinformation from the external controller through the nanoantenna pattern formed on the outer surface of the drug delivery system, an external controller configured to wirelessly receive the bioinformation from the transmission module and wirelessly transmit the drug releasing signal corresponding to the bioinformation to the receiving module, and a power supply configured to supply power to the transmission module for the wireless transmission.

In accordance with still another aspect of the present invention, a thermotherapy device using a thermotherapy complex includes the thermotherapy complex of the present invention, a biosensor located on an outer surface of the thermotherapy complex and configured to detect bioinformation of the inside of a living body, a transmission module configured to receive the bioinformation from the biosensor and wirelessly transmit the bioinformation to an external controller through a nanoantenna pattern formed on the outer surface of the thermotherapy complex, a receiving module configured to wirelessly receive a nanowire releasing signal corresponding to the bioinformation from the external controller through the nanoantenna pattern formed on the outer surface of the thermotherapy complex, an external controller configured to wirelessly receive the bioinformation from the transmission module and wirelessly transmit the nanowire releasing signal corresponding to the bioinformation to the receiving module, and a power supply configured to supply power to the transmission module for the wireless transmission.

DETAILED DESCRIPTION OF EXEMPLARY EMBODIMENTS

The present invention relates to a structure including a porous micro-container, and a nanoantenna pattern formed on an outer surface of the porous micro-container.

Hereinafter, a structure of the present invention will be described in detail with reference to the accompanying drawings.

Figure 1:
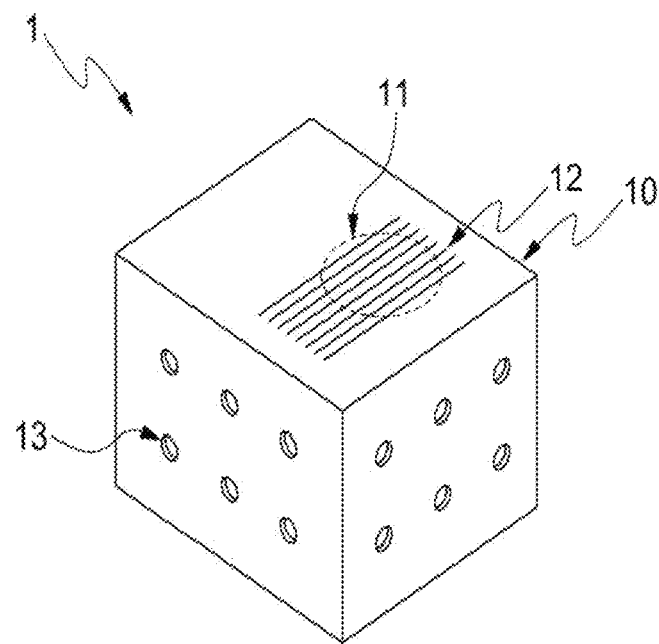
FIG. 1 is a perspective view showing a structure in accordance with an embodiment of the present invention.

FIG. 1 is a perspective view showing a structure in accordance with an embodiment of the present invention. As shown in FIG. 1, a structure 1 of the present invention may include a porous micro-container 10 having pores 13, and a nanoantenna pattern 11 formed on an outer surface of the porous micro-container 10. The nanoantenna pattern 11 may be formed to have an array of one or more nanoantennas 12.

Although the porous micro-container is described as a hexahedron in FIG. 1, the shape of the porous micro-container of the present invention is not limited thereto, and any shape which has a volume in which a material is impregnated may be adopted without restriction. The porous micro-container is described, for example, as having the shape of a polyhedron surrounded by a plurality of surfaces, a sphere, or a cylinder, in the present invention, but is not limited thereto. The polyhedron, the sphere, and the cylinder may include not only a shape in a mathematical sense, but also a shape similar to the shape. That is, for example, the sphere may include a shape similar to a sphere as well as a perfect sphere, and the cylinder may include a shape similar to a cylinder as well as a perfect cylinder. The polyhedron may refer to a shape that is surrounded by four or more surfaces and able to form volume.

In the present invention, a basic framework of the porous micro-container, that is, a main material of the porous micro-container is not particularly limited, and any material which has magnetic properties may be employed without limitation. In the present invention, for example, at least one metal selected from the group consisting of Ni, Fe, Cu, Zn, Au, an alloy thereof, and a metal coated with Au or a parylene polymer, and preferably Au, which is harmless to the human body, may be used as the basic framework of the porous micro-container, but is not limited thereto. Since the parylene has insulating properties, corrosion resistant properties, hydrophobic properties, and biocompatibility, and is not harmful to the human body like Au, the kind of the metal coated with Au or parylene may not be specifically limited, and a normal metal or a metal alloy may be used.

Since the porous micro-container of the present invention consists of a magnetic material, it is possible to move and control the porous micro-container in an electromagnetic field.

A solder hinge may be attached to an inner edge, that is, a boundary at which two inner surfaces meet, of the porous micro-container of the present invention. In the present invention, when manufacturing the porous micro-container, self-assembly of the porous micro-container is possible using surface tension of the solder [Park, J., Slanac, D., Leong, T., Ye, H., and Gracias, D. H., 'Reconfigurable microfluidics with metallic containers,' IEEE MEMS, 2008, 17 (2), pp. 265-271].

A volume of the porous micro-container of the present invention may be 10 $\mu m^3$ to 64,000,000 $\mu m^3$, preferably 10 $\mu m^3$ to 1,000 $\mu m^3$, and more preferably 50 $\mu m^3$ to 100 $\mu m^3$. When the volume of the porous micro-container is less than 10 $\mu m^3$, the amount of impregnation of the pharmaceutically active ingredient or nanowires, which will be described later, may be too small, and when the volume of the porous micro-container is more than 64,000,000 $\mu m^3$, movement in a living body may not be smooth due to a large fluid resistance.

The porous micro-container of the present invention may have pores as shown in FIG. 1, and the average diameter of the pores is 0.1 $\mu m$ to 50 $\mu m$, preferably 0.2 $\mu m$ to 30 $\mu m$, and more preferably 0.5 $\mu m$ to 20 $\mu m$. In the present invention, impregnation and release of the pharmaceutically active ingredient or nanowires, which will be described later, through the pores may be smoothly performed by controlling the average diameter of the pores to be within the above described range.

The structure of the present invention may include the nanoantenna pattern formed on the outer surface of the porous micro-container that allows remote control through an external wireless signal.

The nanoantenna pattern of the present invention may be formed to have an area of 0.01 $\mu m^2$ to 0.5 $\mu m^2$, preferably 0.03 $\mu m^2$ to 0.3 $\mu m^2$, and more preferably 0.05 $\mu m^2$ to 0.1 $\mu m^2$ on the outer surface of the porous micro-container, but is not limited thereto.

The nanoantenna pattern of the present invention may be formed to have the array of one or more nanoantennas. A width, length, and height of the nanoantenna may be respectively 10 nm to 300 nm, 10 $\mu m$ to 300 $\mu m$, and 10 nm to 300 nm, but are not limited thereto. In the present invention, since the width, length, and height of the nanoantenna are controlled to be within the above described range, various ranges of radio frequency depending on a size of the antenna may be transmitted and received through the antennas having various sizes.

The one or more nanoantennas configuring the nanoantenna pattern of the present invention may be arranged at regular intervals, and the regular intervals may be preferably, but not specifically limited to, 10 nm to 300 nm. In the present invention, since the nanoantenna pattern is formed by arranging the nanoantennas at regular intervals of 10 nm to 300 nm, the nanoantenna pattern may resonate at desired radio frequency, and thereafter have compatibility with other high-frequency devices.

Anything that transmits and receives an external wireless signal may be employed as a material of the nanoantenna of the present invention without limitation. The nanoantenna of the present invention may include a conductive material.

The conductive material of the present invention may be a metal material or a magnetic material. The metal material of the present invention may be at least one selected from the group consisting of Al, Pt, Pd, Ag, Cu, Au, and an alloy including one or more of these elements, and the magnetic material may be at least one metal selected from the group consisting of Fe, Co, Ni, and Gd, an alloy including the metal, or an oxide of the metal, but is not limited thereto. The alloy may be anything that includes at least one of the metal material or the magnetic material, without limitation.

The nanoantenna of the present invention may be an omnidirectional antenna and have all directionality similar to a circle on a horizontal plane of an electric field, but is not limited thereto.

The nanoantenna of the present invention may transmit and receive a radio frequency (RF) of 0.5 GHz to 40 GHz, and preferably 7.5 GHz to 13.4 GHz, but is not limited thereto. In the present invention, when the frequency of the RF is lower than 0.5 GHz, a compatibility problem with other high-frequency devices may occur since the frequency is too low, and when the frequency of the RF is higher than 40 GHz, the compatibility problem with other high-frequency devices may also occur since the frequency is too high.

In the present invention, a bandwidth of the nanoantenna may include a resonant frequency of the nanoantenna. By using the bandwidth including the resonant frequency of the nanoantenna, effects of drug therapy and thermotherapy, which will be described later, may be maximized.

In addition, when the resonant frequency is set as a centre frequency, the bandwidth of the nanoantenna in the present invention may reach up to 60% of the centre frequency. That is, the nanoantenna may appropriately react to an electromagnetic wave that reacts in a bandwidth within 60% of the resonant frequency.

The structure of the present invention may further include the dielectric layer formed between the outer surface of the porous micro-container and the nanoantenna pattern. The dielectric layer of the present invention may insulate the nanoantenna pattern from the porous micro-container, and thereby help the nanoantenna pattern to function as an independent electronic module.

Figure 2:
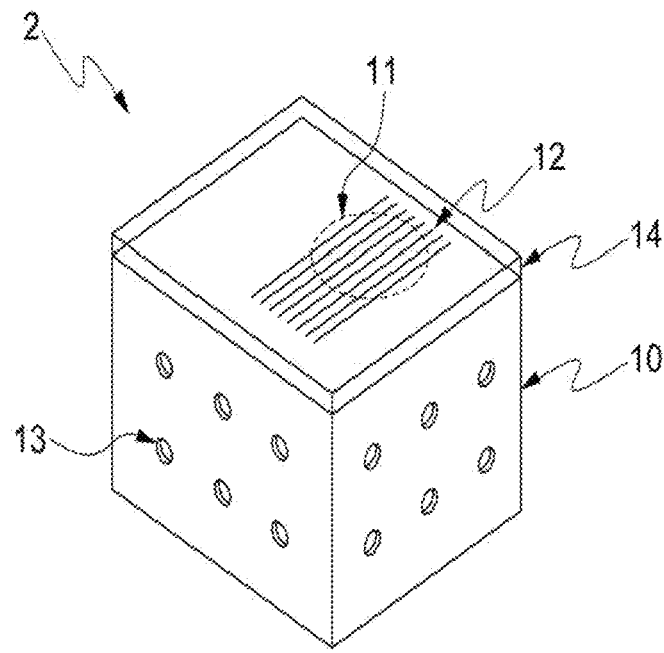
FIG. 2 is a perspective view showing a structure in accordance with another embodiment of the present invention.

FIG. 2 is a perspective view showing a structure in accordance with another embodiment of the present invention. As shown in FIG. 2, the structure 2 of the present invention may include a porous micro-container 10 having pores 13, a dielectric layer 14 formed on an outer surface of the porous micro-container 10, and a nanoantenna pattern 11 disposed on the dielectric layer 14. The nanoantenna pattern 11 may be formed to have an array of one or more nanoantennas 12.

In the present invention, a thickness of the dielectric layer may be 10 nm to 300 nm, and preferably 150 nm to 250 nm, but is not limited thereto. In the present invention, when the dielectric layer has a thickness of less than 10 nm, it is so thin that an insulating effect is negligible due to a breakdown from defect in the dielectric layer or high electric field formation, and when the dielectric layer has a thickness of more than 300 nm, it is so thick that mechanical damage may occur.

In the present invention, the type of the dielectric layer is not particularly limited, and anything that has good insulating properties may be used without limitation. In the present invention, for example, silicon oxide, silicon nitride, or polymers which have excellent insulating properties, corrosion resistant properties, hydrophobic properties, and biocompatibility, such as a parylene polymer, may be used as the dielectric layer, but the dielectric layer is not limited thereto.

The present invention also relates to a method of manufacturing a structure, which includes forming a nanoantenna pattern on an outer surface of the porous micro-container using a focused ion beam (FIB) system.

In the method of manufacturing a structure, specific details of the porous micro-container and the nanoantenna pattern may be the same as described above.

Figure 3:
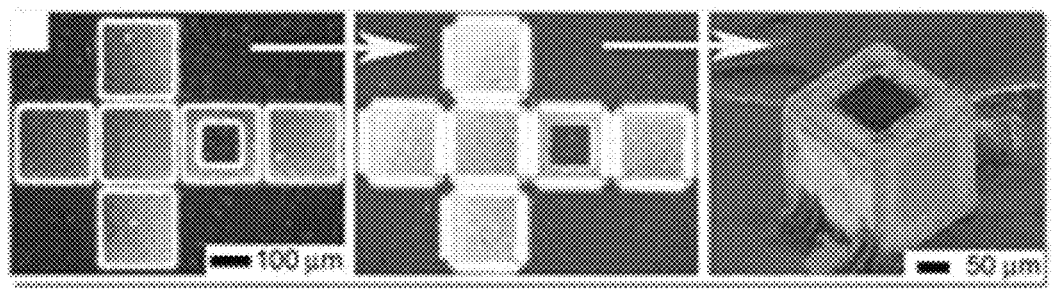
FIG. 3 is a schematic diagram showing a process of manufacturing or preparing a porous micro-container in accordance with an embodiment of the present invention.

To manufacture a structure of the present invention, firstly, a porous micro-container may be fabricated or prepared. FIG. 3 is a diagram showing a process of manufacturing or preparing a porous micro-container in accordance with an embodiment of the present invention.

In the present invention, to fabricate or prepare the porous micro-container, a two-dimensional (planar) metal frame may be formed using a photolithography process [Park, J., Slanac, D., Leong, T., Ye, H., and Gracias, D. H., 'Reconfigurable microfluidics with metallic containers,' IEEE MEMS, 2008, 17 (2), pp. 265-271]. The metal frame may be a basic framework of the porous micro-container, and at least one metal selected from the group consisting of Ni, Fe, Cu, Zn, and Au, but is not limited thereto.

After the two-dimensional (planar) metal frame is formed, solder hinges may be attached to all edges of the metal frame, and the solder may be liquefied by heating. The porous micro-container may be self-assembled using surface tension of the liquefied solder [Leong, T., Lester, P. A., Koh, T. L., Call, E. K., and Gracias, D. H., 'Surface tension-driven self-folding polyhedra,' Langmuir, 2007, 23, pp. 8747-8751].

In the present invention, in order to provide porosity to the porous micro-container, pores may be formed in a metal surface while forming the two-dimensional (planar) metal frame using the photolithography process.

Figure 4:
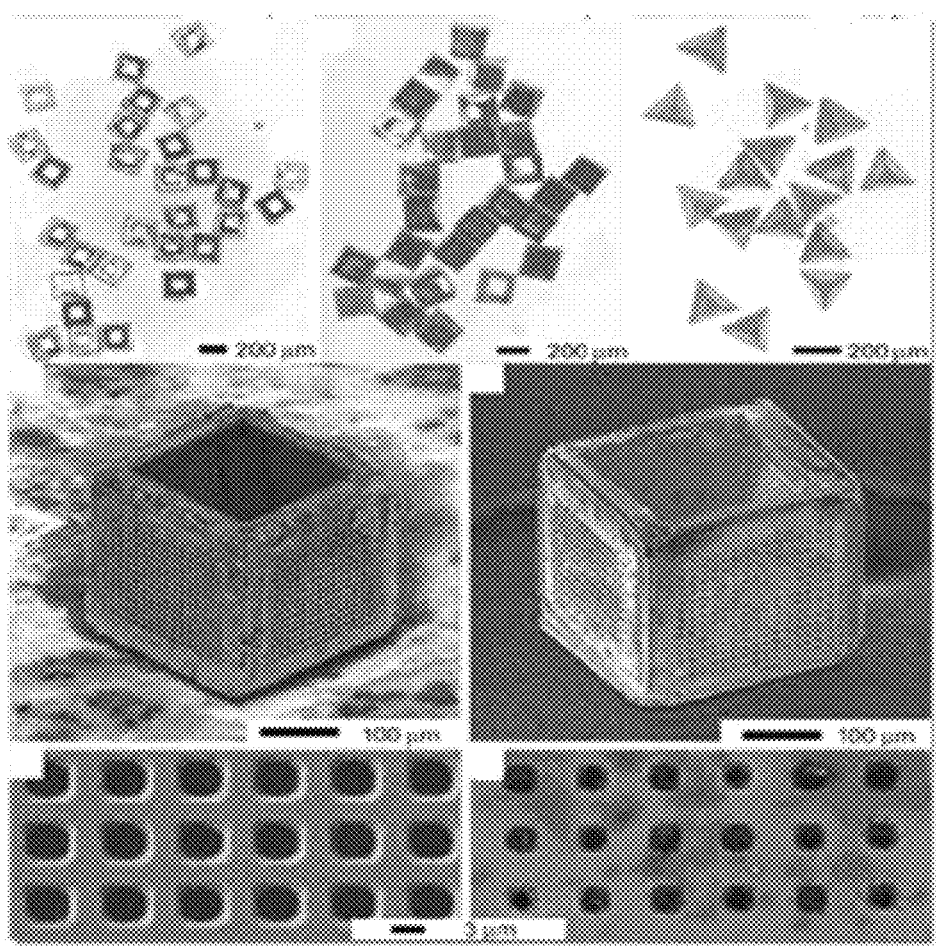
FIG. 4 is a view showing various shapes and pores of a porous micro-container in accordance with another embodiment of the present invention.

FIG. 4 is a view showing various shapes and pores of a porous micro-container in accordance with an embodiment of the present invention.

After manufacturing or preparing the porous micro-container in accordance with the present invention, as described above, a nanoantenna pattern may be formed on an outer surface of the porous micro-container using an FIB system.

A nanolithographic process using e-beam lithography in the related art is a top-down process, and there is a disadvantage in that an additional removal process is required in addition to a deposition process. However, since the FIB system is for manufacturing a nano-structure, the nano-structure may be directly formed even on a three-dimensional material such as a micro-container. Although the FIB system is widely known in the microelectronics field [Reyntjens, S., and Puers, R., 'A review of focused ion beam applications in microsystem technology,'J. Micromech. Microeng. 2001, 11, pp. 287-300], the FIB system process of forming the nanoantenna on the outer surface of the porous micro-container, as shown in the present invention, was first developed by the inventors of the present invention.

In the present invention, specifically, the conductive material may be deposited on the outer surface of the porous micro-container by injecting a gas including a conductive material, which is to form the nanoantenna, for example, a $Pt(CH_3)_3$ gas including Pt, while irradiating a gallium ion beam having an energy of 20 keV to 30 keV and a diameter of about 5 nm to 20 nm to the outer surface of the porous micro-container. Additional information about the conductive material is the same as described above.

During the deposition process, current of the gallium ion beam may be 0.2 pA to 1000 pA, but is not limited thereto.

In order to form the nanoantenna pattern through the deposition process, the porous micro-container may be exposed to the gas including the gallium ion beam and conductive material for 100 seconds to 500 seconds, but is not limited thereto.

The method of manufacturing the structure of the present invention may further include forming a dielectric layer on the outer surface of the porous micro-container before forming the nanoantenna pattern on the outer surface of the porous micro-container.

In the present invention, by forming the nanoantenna pattern on the dielectric layer after forming the dielectric layer on the outer surface of the porous micro-container, the nanoantenna pattern may be insulated from the porous micro-container to function as an independent electronic module.

In the method of manufacturing the structure of the present invention, specific information about the dielectric layer is the same as described above.

In the present invention, the formation of the dielectric layer on the outer surface of the porous micro-container may be performed using a plasma enhanced chemical vapor deposition (PECVD) process, but is not limited thereto.

Figure 5:
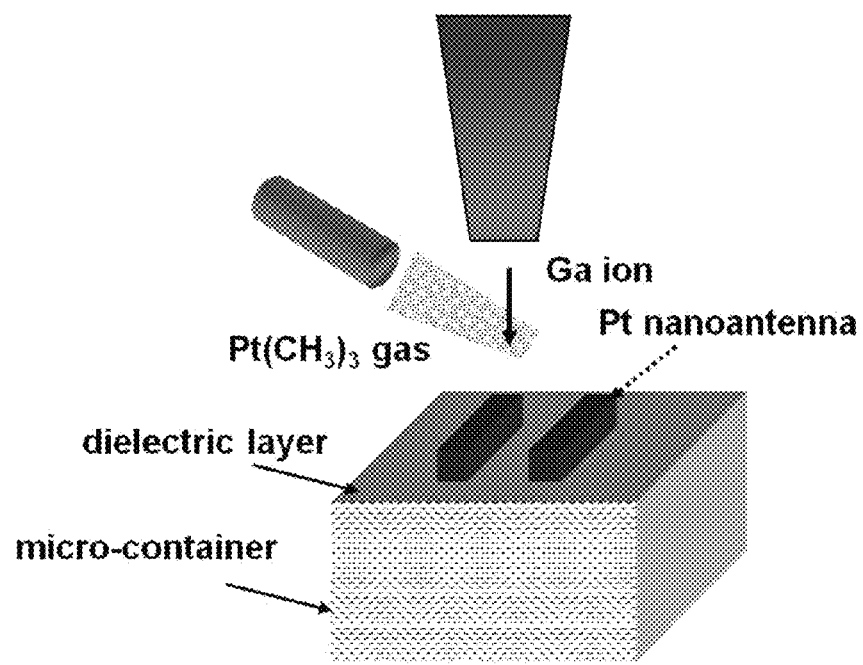
FIG. 5 is a schematic diagram showing a process of forming a dielectric layer on an outside of a porous micro-container and forming a nanoantenna pattern on the dielectric layer using a focused ion beam (FIB) system in accordance with an embodiment of the present invention.

FIG. 5 is a schematic diagram showing a process of forming a dielectric layer on the outside of the porous micro-container and forming the nanoantenna pattern on the dielectric layer using the FIB system in accordance with an embodiment of the present invention.

Further, the present invention relates to a drug delivery system which includes the structure of the above-described present invention, and a pharmaceutically active ingredient impregnated in the porous micro-container of the structure.

Since the drug delivery system of the present invention uses the above-described structure of the present invention, a drug may be released from a desired region inside the living body at a desired time.

Specifically, since the drug delivery system of the present invention makes use of the structure of the present invention, the drug delivery system may receive a radio frequency transmitted from outside through the nanoantenna pattern of the structure. When the nanoantenna pattern of the structure receives the external radio frequency, heat may be generated. The heat generated from the nanoantenna pattern may be transferred to the inside of the porous micro-container to release the pharmaceutically active ingredient impregnated in the porous micro-container to the outside.

Accordingly, when the drug delivery system of the present invention is located at a desired region of the living body, for example, at cancer tissues, and a radio frequency which the nanoantenna pattern is able to receive is transmitted from the outside at a desired time, the pharmaceutically active ingredient impregnated in the porous micro-container may be released and an therapeutic effect of cancer cell may be obtained.

Various methods well known in the field may be adopted as a method of moving the drug delivery system of the present invention to the desired region inside the living body, with no limitation. In addition, the region inside the living body to which the drug delivery system of the present invention is to be applied is not particularly limited, and any region that needs the drug therapy may be possible.

The kind of the pharmaceutically active ingredient that is introduced into the drug delivery system of the present invention is not particularly limited, and any kind of ingredient well known in the field may be adopted.

In the present invention, the pharmaceutical active ingredient, for example, may be at least one selected from the group consisting of anticancer drugs, antibiotics, hormones, hormone antagonists, interleukin, interferon, growth factors, tumor necrosis factors, endotoxins, lymphotoxins, urokinase, streptokinase, tissue plasminogen active agents, protease inhibitors, alkylphosphocholines, radioisotope markers, surfactants, cardiovascular drugs, gastrointestinal drugs, and neuro drugs, but is not limited thereto In the present invention, the antitumor agent, for example, may be at least one selected from the group consisting of epirubicin, docetaxel, gemcitabine, paclitaxel, cisplatin, carboplatin, taxol, procarbazine, cyclophosphamide, diactinomycin, daunorubicin, etoposide, tamoxifen, doxorubicin, mitomycin, bleomycin, plicomycin, transplatinum, vinblastin, and methotrexate, but is not limited thereto.

A method of introducing the pharmaceutically active ingredient into the structure of the present invention is not particularly limited, and a method of mixing the structure and the pharmaceutically active ingredient in an appropriate solvent, for example, may be introduced.

In addition, the kinds of diseases to which the drug delivery system of the present invention is applied are not particularly limited, and the drug delivery system of the present invention may be applied to gastric cancer, lung cancer, breast cancer, ovarian cancer, liver cancer, bronchial cancer, nasopharyngeal cancer, laryngeal cancer, pancreatic cancer, bladder cancer, colon cancer, cervical cancer, etc. However, uses of the drug delivery system of the present invention are not particularly limited to the above-described diseases, and may be greatly diversified by controlling the pharmaceutically active ingredient included in the drug delivery system.

In the present invention, the pharmaceutically active ingredient may be encapsulated with a hydrogel. Since the drug delivery system of the present invention includes the pharmaceutically active ingredient encapsulated with the hydrogel, it is possible to prevent the pharmaceutically active ingredient from being easily released and control the release time in such a way that the pharmaceutically active ingredient is released at a desired time.

Specifically, since the pharmaceutically active ingredient is encapsulated with the hydrogel in the present invention, the release may not be arbitrary even when the drug delivery system of the present invention is located at the desired region inside the living body.

When a radio frequency is transmitted from the outside at a time that the drug is to be released after disposing the drug delivery system of the present invention at the desired region inside the living body, the nanoantenna pattern of the drug delivery system may receive the radio frequency, and generate heat. The heat generated from the nanoantenna pattern may be transferred to the porous micro-container, and dissolve the hydrogel impregnated thereinside. Accordingly, the pharmaceutically active ingredient encapsulated with the hydrogel may be released through the pores of the porous micro-container.

In the present invention, the kind of the hydrogel encapsulating the pharmaceutically active ingredient is not specifically limited, and anything that melts by heat and has fluidity may be adopted without limitation. In the present invention, for example, gelatin or a pluronic gel may be used as the hydrogel, but the hydrogel is not limited thereto.

A method of introducing the hydrogel into the structure of the present invention is not specifically limited, and, for example, the hydrogel may be introduced into the structure of the present invention by impregnating the pharmaceutically active ingredient in the structure of the present invention, followed by inserting the structure impregnated with the pharmaceutically active ingredient into a container containing the hydrogel.

Further, the present invention relates to a thermotherapy complex including the above-described structure of the present invention, and nanowires impregnated in a porous micro-container of the structure.

Since the thermotherapy complex of the present invention uses the above-described structure of the present invention, a therapeutic effect may be obtained by releasing nanowires from a desired region inside the living body at a desired time, and killing target cells through the nanowires.

The term "thermotherapy (hyperthermia)" used herein may refer to a treatment in which particles that emit heat are inserted to kill target cells with the heat, using the fact that cancer cells, etc. are more vulnerable to the heat than normal cells.

Specifically, since the thermotherapy complex of the present invention uses the structure of the present invention, the thermotherapy complex of the present invention may receive a radio frequency transmitted from the outside through the nanoantenna pattern of the structure. The nanoantenna pattern of the structure may generate heat upon receiving the external radio frequency. The heat generated from the nanoantenna pattern may be transferred into the porous micro-container, and heat the nanowires impregnated in the porous micro-container to be released. The heated nanowires may be attached to target cells inside the living body and kill the target cells using the heat.

Accordingly, when the thermotherapy complex of the present invention is disposed at the desired region inside the living body, for example, at cancer tissues, and a radio frequency which the nanoantenna pattern is able to receive is transmitted from the outside at a time at which thermotherapy is required, the nanowires impregnated in the porous micro-container may be released in a heated state to obtain an therapeutic effect of cancer cells, etc.

Various methods well known in the field may be adopted as a method of moving the thermotherapy complex of the present invention to the desired region inside the living body, with no limitation. In addition, the region inside the living body to which the thermotherapy complex of the present invention is to be applied is not particularly limited, and any region to which the thermotherapy is applied may be possible.

The kind of nanowires that are introduced into the thermotherapy complex of the present invention is not particularly limited, and any kind of conductive material that emits heat may be used without limitation. In the present invention, as an example of the nanowires, at least one metal selected from the group consisting of Fe, Ni, Co, Gd, Ag, Au, Pt, Pd, Zn, and Ti, an alloy including the metal, an oxide of the metal, a nitride of the metal, or a carbide of the metal may be used, but the nanowires are not limited thereto. The alloy may be anything that includes at least one of the metals without limitation.

A method of introducing the nanowires into the structure of the present invention is not specifically limited, and a method of mixing the structure and the nanowires in an appropriate solvent, for example, may be used.

In addition, the kinds of diseases to which the thermotherapy complex of the present invention is applied is not particularly limited, and the thermotherapy complex of the present invention may be applied to gastric cancer, lung cancer, breast cancer, ovarian cancer, liver cancer, bronchial cancer, nasopharyngeal cancer, laryngeal cancer, pancreatic cancer, bladder cancer, colon cancer, cervical cancer, etc. However, uses of the thermotherapy complex of the present invention are not limited to the above-described diseases, and may be greatly diversified in the thermotherapy field.

In the present invention, the nanowires may be encapsulated with a hydrogel. Since the thermotherapy complex of the present invention uses the nanowires encapsulated with the hydrogel, it is possible to prevent the nanowires from being easily released from the thermotherapy complex and control the release time in such a way that the nanowires are released at a desired time.

Specifically, since the thermotherapy complex of the present invention encapsulates the nanowires with the hydrogel, the release may not be arbitrary even when the thermotherapy complex of the present invention is located at the desired region inside the living body.

When the thermotherapy complex of the present invention is disposed at the desired region inside the living body, and a radio frequency is transmitted from the outside at a time at which the thermotherapy is required, the nanoantenna pattern of the thermotherapy complex may receive the radio frequency and generate heat. The heat generated from the nanoantenna pattern may be transferred to the porous micro-container, and dissolve the hydrogel impregnated thereinside. Accordingly, the nanowires encapsulated with the hydrogel may be released through the pores of the porous micro-container. Since the nanowires are heated by the heat transferred from the nanoantenna pattern, released through the pores, and attached to target cells, for example, cancer cells, a thermotherapy effect in which the nanowires induce the cancer cells to be killed by the heat can be achieved.

In the present invention, the specific kind of the hydrogel encapsulating the nanowires is not particularly limited, and anything that melts by heat and has fluidity may be adopted without limitation. In the present invention, for example, gelatin or a pluronic gel may be used as the hydrogel, but the hydrogel is not limited thereto.

A method of introducing the hydrogel into the structure of the present invention is not specifically limited, and, for example, the hydrogel may be introduced into the structure of the present invention by impregnating the nanowires in the structure of the present invention, followed by inserting the structure impregnated with the nanowires to a container containing the hydrogel.

Further, the present invention relates to a drug therapy device using a drug delivery system including the above-described drug delivery system of the present invention, a biosensor located on an outer surface of the drug delivery system and configured to detect bioinformation of the inside of a living body, a transmission module configured to receive the bioinformation from the biosensor and wirelessly transmit the bioinformation to an external controller through a nanoantenna pattern formed on the outer surface of the drug delivery system, a receiving module configured to wirelessly receive a drug releasing signal corresponding to the bioinformation from the external controller through the nanoantenna pattern formed on the outer surface of the drug delivery system, an external controller configured to wirelessly receive the bioinformation from the transmission module and wirelessly transmit the drug releasing signal corresponding to the bioinformation to the receiving module, and a power supply configured to supply power to the transmission module for the wireless transmission.

The drug therapy device of the present invention may perform drug therapy appropriate to a biological environment, in such a way that the above-described drug delivery system receives the bioinformation from the inside of the living body to be transmitted to the external controller, and the external controller analyzes the bioinformation and transmits the drug releasing signal corresponding to the bioinformation to the drug delivery system.

The drug delivery system included in the drug therapy device of the present invention may be the same as that described above.

The drug therapy device of the present invention may include the bio sensor which is located on the outer surface of the drug delivery system and configured to detect the bioinformation from the inside of the living body. The biosensor may detect a variety of bioinformation of the inside of the living body, for example, variations in pH or specific chemical materials of the inside of the living body. In the present invention, the specific kind of the biosensor is not particularly limited, and, for example, may be a pH sensor, a sensor configured to detect a specific chemical material, or a micro-camera configured to take a picture of an image or video, etc.

The drug therapy device of the present invention may include the transmission module which receives the bioinformation from the biosensor and wirelessly transmits the bioinformation to the external controller, through the nanoantenna pattern formed on the outer surface of the drug delivery system.

In addition, the drug therapy device of the present invention may include the receiving module which wirelessly receives the drug releasing signal corresponding to the bioinformation from the external controller, through the nanoantenna pattern formed on the outer surface of the drug delivery system.

The drug therapy device of the present invention may include the external controller which wirelessly receives the bioinformation from the transmission module and wirelessly transmits the drug releasing signal corresponding to the bioinformation to the receiving module. Since the external controller receives the bioinformation of the inside of the living body, analyzes the bioinformation, and transmits the drug releasing signal corresponding to the bioinformation to the receiving module, communication between the external controller and the drug delivery system may be possible. That is, the nanoantenna pattern of the present invention may transmit and receive a radio frequency, and thereby communicate with the external controller.

The drug therapy device of the present invention may include the power supply configured to supply power to the transmission module to perform wireless transmission. The power supply may be a microchip-type cell or biofuel cell attached to the outer surface of the drug delivery system of the present invention, or may obtain energy from the outside of the living body through electromagnetic waves.

In the drug therapy device of the present invention, when the biofuel cell attached to the outer surface of the drug delivery system is used as the power supply, the biofuel cell may generate electricity using glucose which is a biofuel present inside the living body.

Further, the present invention relates to a thermotherapy device using a thermotherapy complex including the above-described thermotherapy complex of the present invention, a biosensor located on an outer surface of the thermotherapy complex and configured to detect bioinformation of the inside of a living body, a transmission module configured to receive the bioinformation from the biosensor and wirelessly transmit the bioinformation to an external controller through a nanoantenna pattern formed on the outer surface of the thermotherapy complex, a receiving module configured to wirelessly receive a nanowire releasing signal corresponding to the bioinformation from the external controller through the nanoantenna pattern formed on the outer surface of the thermotherapy complex, an external controller configured to wirelessly receive the bioinformation from the transmission module and wirelessly transmit the nanowire releasing signal corresponding to the bioinformation to the receiving module, and a power supply configured to supply power to the transmission module for the wireless transmission.

The thermotherapy device of the present invention may perform thermotherapy appropriate to the biological environment in such a way that the above-described thermotherapy complex receives bioinformation from the inside of the living body and transmits the bioinformation to the external controller, and the external controller analyzes the bioinformation and transmits the nanowire releasing signal corresponding to the bioinformation to the thermotherapy complex.

The thermotherapy complex included in the thermotherapy device of the present invention may be the same as that described above.

The thermotherapy device of the present invention may include the biosensor which is located on the outer surface of the thermotherapy complex and configured to detect the bioinformation of the inside of the living body. The biosensor may detect a variety of bioinformation of the inside of the living body, for example, a variation in pH or a specific chemical material of the inside of the living body. In the present invention, the specific kind of the biosensor is not particularly limited, and, for example, may be a pH sensor, a sensor configured to detect a specific chemical material, or a micro-camera configured to take a picture of an image or video, etc.

The thermotherapy device of the present invention may include the transmission module which receives the bioinformation from the biosensor and wirelessly transmits the bioinformation to the external controller through a nanoantenna pattern formed on an outer surface of the thermotherapy complex.

In addition, the thermotherapy device of the present invention may include the receiving module which wirelessly receives the nanowire releasing signal corresponding to the bioinformation from the external controller through the nanoantenna pattern formed on the outer surface of the thermotherapy complex.

The thermotherapy device of the present invention may include the external controller which wirelessly receives the bioinformation from the transmission module and wirelessly transmits the nanowire releasing signal corresponding to the bioinformation to the receiving module. Since the external controller receives the bioinformation of the inside of the living body, analyzes the bioinformation, and transmits the nanowire releasing signal corresponding to the bioinformation to the receiving module, communication between the external controller and the thermotherapy complex may be possible. That is, the nanoantenna pattern of the present invention may transmit and receive a radio frequency, and thereby communicate with the external controller.

The thermotherapy device of the present invention may include the power supply configured to supply power to the transmission module to perform wireless transmission. The power supply may be a microchip-type cell or biofuel cell attached to the outer surface of the thermotherapy complex of the present invention, or may obtain energy from the outside of the living body through electromagnetic waves.

In the thermotherapy device of the present invention, when the biofuel cell attached to the outer surface of the thermotherapy complex is used as the power supply, the biofuel cell may generate electricity using glucose which is a biofuel present inside the living body.

Hereinafter, the present invention will be described in more detail, referring to embodiments of the present invention and comparative examples not belonging to the present invention. However, it should be noted that the scope of the present invention is not restricted to these embodiments.

Example 1

(1) Fabrication or Preparation of Porous Micro-Container

A two-dimensional Ni basic framework having an average diameter of 50 μm in a planar cross shape was fabricated using a photolithography process, as shown in FIG. 3(a).

Next, as shown in FIG. 3(b), a solder hinge was attached to all of the edges of the Ni basic framework. Next, the Ni basic framework having the solder hinge attached thereto was heated at a temperature of 100° C. for 3 minutes, and to a temperature of 250° C. for 3 minutes to liquefy the solder, and a porous micro-container was self-assembled using surface tension of the liquefied solder, as shown in FIG. 3(c). The volume of the porous micro-container was 64,000,000 $\mu m^3$.

(2) Formation of Dielectric Layer on Porous Micro-Container

A dielectric layer was formed by coating silicon oxide having a thickness of 200 nm on an outer surface of the prepared porous micro-container using a plasma enhanced chemical vapor deposition (PECVD) process.

(3) Formation of Nanoantenna Pattern on Dielectric Layer

A nanoantenna pattern was formed on the formed dielectric layer using an FIB system. Specifically, the nanoantenna pattern having an area of about 0.07 $\mu m^2$ was formed on the dielectric layer by passing $Pt(CH_3)_3$ gas including a conductive material (Pt) for 300 seconds using a gallium ion beam, while radiating the gallium ion beam having an energy of 25 keV, beam current of 50 picoAmpere (pA) and a diameter of 10 nm on the dielectric layer formed on the outer surface of the porous micro-container. Each of nanoantennas configuring the nanoantenna pattern has a size of 80 nm×100 μm×100 nm (width×length×height), and the nanoantennas were arranged at regular intervals of 100 nm.

Accordingly, a structure including the porous micro-container, the dielectric layer formed on the outer surface of the porous micro-container, and the nanoantenna pattern formed on the dielectric layer was formed.

Figure 6:
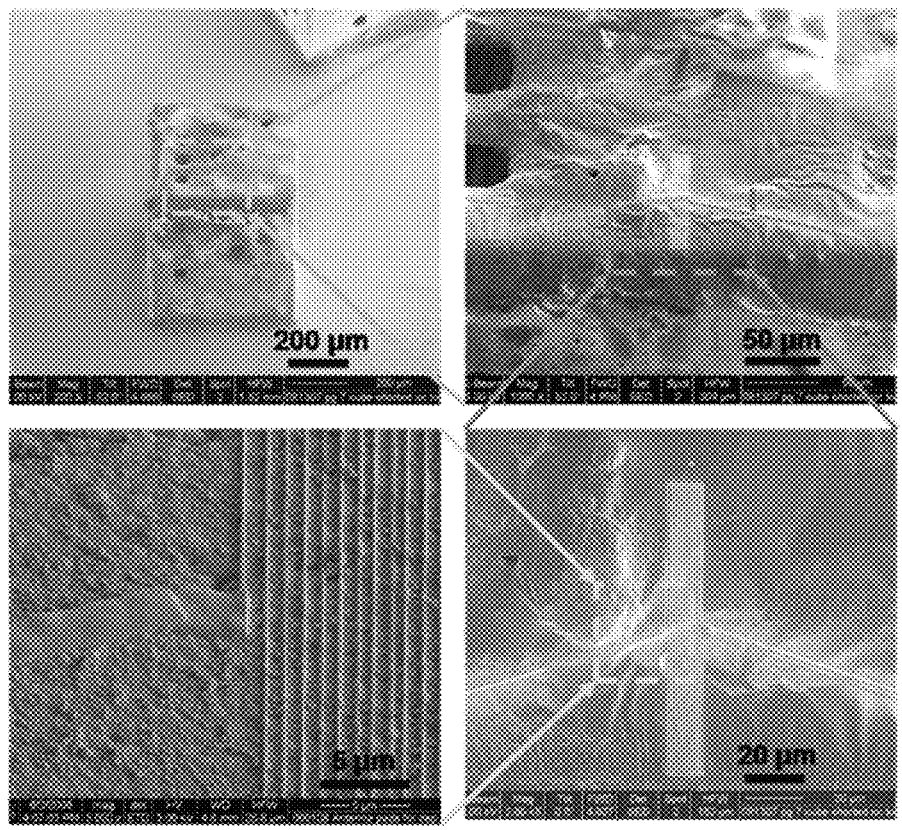
FIG. 6 shows photographs gradually enlarging a field emission scanning microscope (FESEM) image of the structure shown in FIG. 5.

FIG. 6 shows photographs gradually enlarging a field emission scanning microscope (FESEM) image of the structure. As shown in FIG. 6, when enlarging the nanoantenna in a clockwise direction from an upper left portion, it may be found that the nanoantennas are arranged at regular intervals to form a nanoantenna pattern.

Experimental Example 1

In order to confirm radio frequency characteristics of the structure fabricated in Example 1, High Frequency Structure Simulator (HFSS, Anson Corp.), which is a high frequency electromagnetic simulator, was used.

Figure 7:
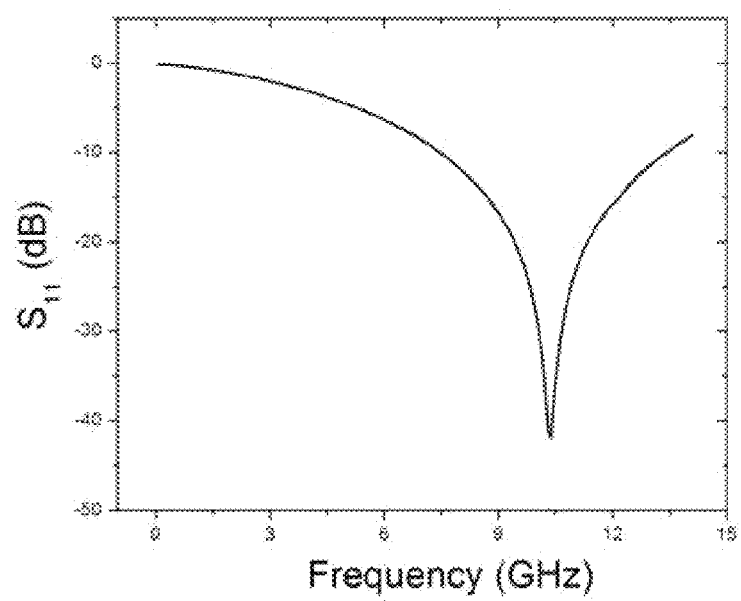
FIG. 7 is a graph showing a reflection mode $S_{11}$ of a structure in accordance with an embodiment of the present invention, which is measured using a high frequency structural simulator (HFSS).

FIG. 7 is a graph showing a reflection mode $S_{11}$ of the structure, which is measured using the HFSS. The reflection mode was analyzed using microwaves having a frequency of 100 MHz to 14 GHz. As shown in FIG. 7, the nanoantenna pattern of Example 1 shows a resonance frequency of 10.8 GHz, and a return loss of −10 dB within a frequency range of 7.5 GHz to 13.4 GHz. A bandwidth of the nanoantenna pattern is 49.3% with a center frequency of 10.8 GHz, when compared to the frequency range of 7.5 GHz to 13.4 GHz.

Figure 8:
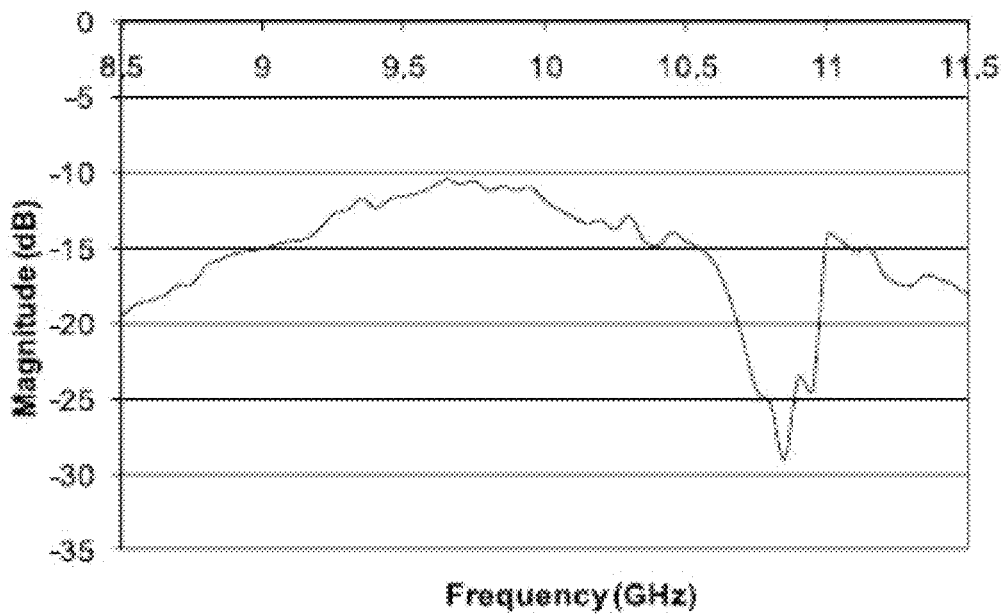
FIG. 8 is a graph showing an S-parameter experimental analysis of a structure in accordance with an embodiment of the present invention, which is measured using a vector network analyzer (VNA, Agilent 8720 ES).

FIG. 8 is a graph showing S-parameter experimental analysis of a structure in accordance with an embodiment of the present invention, which is measured using a vector network analyzer (VNA, Agilent 8720 ES). The standard experimental setup was carried out based on a vector network analyzer (VNA) and microstrip line connection for high frequency characteristics. The microstrip line connection was measured using a ground-signal-ground probe. As shown in FIG. 8, the resonance frequency was about 10.8 GHz, and the return loss was −29 dB. A standing wave ratio at peak was 1.01, and an ideal impedance matching was obtained. Loss difference from the measured result was induced due to the impedance matching with an external circuit.

Figure 9:
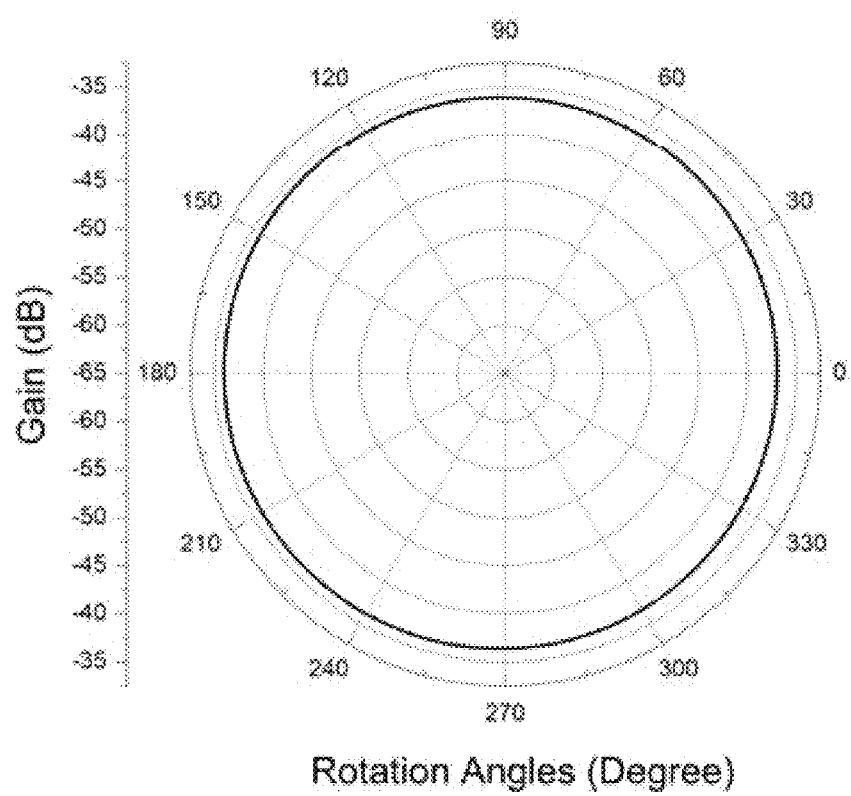
FIG. 9 is a diagram showing magnetization characteristics of a structure on an electric field plane in accordance with an embodiment of the present invention.

FIG. 9 is a diagram showing magnetization characteristics of a structure of the present invention on an electric field plane. As shown in FIG. 9, the nanoantenna pattern included in the structure of the present invention shows characteristics of an omnidirectional antenna, and a null is shown at 90° position, similar to a single dipole antenna.

Figure 10:
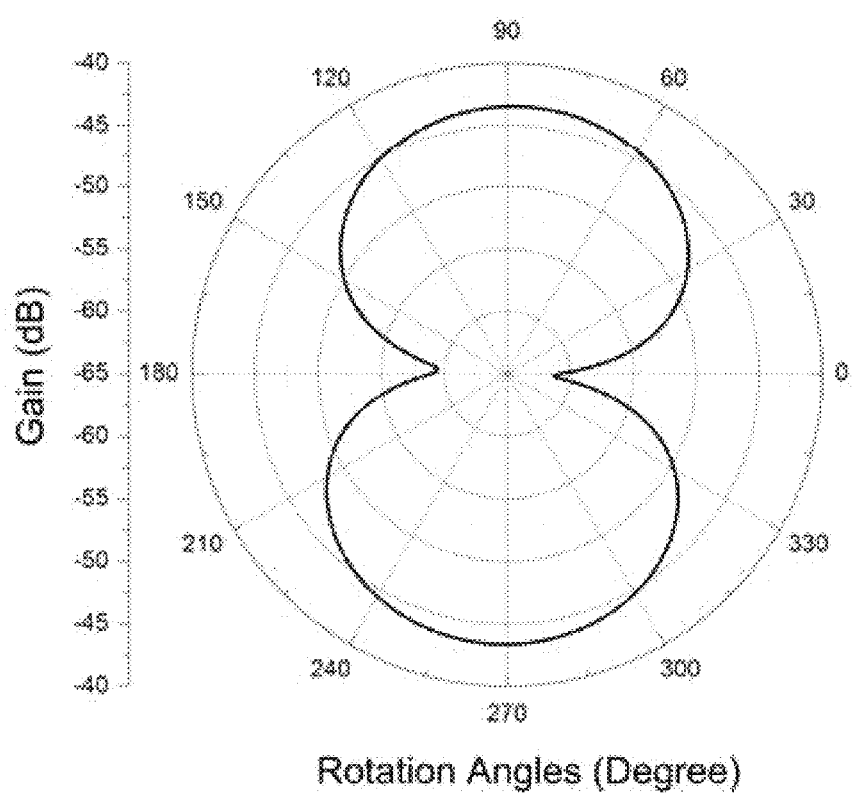
FIG. 10 is a diagram showing magnetization characteristics of a structure on a magnetic field plane in accordance with an embodiment of the present invention.

FIG. 10 is a diagram showing magnetization characteristics of a structure of the present invention on a magnetic field plane. As shown in FIG. 10, the nanoantenna pattern included in the structure of the present invention shows characteristics of a wide band microwave antenna, a centre frequency may move to a lower frequency, and antenna gain may be improved by manufacturing the nanoantenna pattern to have a longer periodic pattern.

A structure of the present invention, which has a nanoantenna pattern formed on an outer surface of a porous micro-container, may be wirelessly controlled from outside. When the structure is used as a drug delivery system and a thermotherapy complex, it is possible to apply drug therapy and thermotherapy to a desired area inside a living body at any time. In addition, the structure of the present invention, which can transmit/receive a wireless signal to/from an external controller through a nanoantenna, may be used as the drug therapy device and the thermotherapy device by detecting a signal from the inside of the living body to be transmitted to the external controller, and releasing a drug or nanowires depending on a corresponding signal transmitted from the external controller.

The structure of the present invention may be used as a drug delivery system, a drug delivery device, or a thermotherapy device.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A structure, comprising:
a porous micro-container, wherein a basic framework of the porous micro-container consists of at least one metal selected from the group consisting of Ni, Fe, Cu, Zn, Au, an alloy thereof, and a metal coated with Au or a parylene polymer;
a nanoantenna pattern formed on an outer surface of the porous micro-container,
wherein the nanoantenna pattern is formed to have an array of one or more nanoantennas which are arranged at regular intervals; and
a dielectric layer formed between the outer surface of the porous micro-container and the nanoantenna pattern, wherein the dielectric layer is prepared from silicon oxide, silicon nitride, or a parylene polymer.

2. The structure of claim 1, wherein a solder hinge is attached to an inner edge of the porous micro-container.

3. The structure of claim 1, wherein the volume of the porous micro-container is 10 $\mu m^3$ to 64,000,000 $\mu m^3$.

4. The structure of claim 1, wherein the regular intervals are 10 nm to 300 nm.

5. The structure of claim 1, wherein the nanoantenna includes a conductive material.

6. The structure of claim 1, wherein a bandwidth of the nanoantenna includes a resonant frequency of the nanoantenna.

7. A drug delivery system, comprising:
a structure of claim 1; and
a pharmaceutically active ingredient impregnated in a porous micro-container of the structure.

8. The drug delivery system of claim 7, wherein the pharmaceutically active ingredient is encapsulated with a hydrogel.

9. A thermotherapy complex, comprising:
a structure of claim 1; and
nanowires impregnated in a porous micro-container of the structure.

10. The thermotherapy complex of claim 9, wherein the nanowires are at least one metal selected from the group consisting of Fe, Ni, Co, Gd, Ag, Au, Pt, Pd, Zn, and Ti, an alloy including the metal, an oxide of the metal, a nitride of the metal, or a carbide of the metal.

11. The thermotherapy complex of claim 9, wherein the nanowires are encapsulated with a hydrogel.

12. A drug therapy device using a drug delivery system, comprising:
a drug delivery system of claim 7;
a biosensor located on an outer surface of the drug delivery system and configured to detect bioinformation of the inside of a living body;
a transmission module configured to receive the bioinformation from the biosensor and wirelessly transmit the bioinformation to an external controller through a nanoantenna pattern formed on the outer surface of the drug delivery system;
a receiving module configured to wirelessly receive a drug releasing signal corresponding to the bioinformation from the external controller through the nanoantenna pattern formed on the outer surface of the drug delivery system;
an external controller configured to wirelessly receive the bioinformation from the transmission module and wirelessly transmit the drug releasing signal corresponding to the bioinformation to the receiving module; and
a power supply configured to supply power to the transmission module for the wireless transmission.

13. The drug therapy device of claim 12, wherein the power supply is a microchip-type cell or a biofuel cell attached to the outer surface of the drug delivery system, or obtains energy from the outside of the living body through electromagnetic waves.

14. A thermotherapy device using a thermotherapy complex, comprising:
a thermotherapy complex of claim 9;
a biosensor located on an outer surface of the thermotherapy complex and configured to detect bioinformation of the inside of a living body;
a transmission module configured to receive the bioinformation from the biosensor and wirelessly transmit the bioinformation to an external controller through a nanoantenna pattern formed on the outer surface of the thermotherapy complex;
a receiving module configured to wirelessly receive a nanowire releasing signal corresponding to the bioinformation from the external controller through the nanoantenna pattern formed on the outer surface of the thermotherapy complex;
an external controller configured to wirelessly receive the bioinformation from the transmission module and wirelessly transmit the nanowire releasing signal corresponding to the bioinformation to the receiving module; and
a power supply configured to supply power to the transmission module for the wireless transmission.

15. The thermotherapy device of claim 14, wherein the power supply is a microchip-type cell or a biofuel cell attached to the outer surface of the thermotherapy complex, or obtains energy from the outside of the living body through electromagnetic waves.

16. A drug therapy device using a drug delivery system, the drug therapy device comprising:
the drug delivery system that comprises:
a structure that includes:
a porous micro-container, and
a nanoantenna pattern formed on an outer surface of the porous micro-container wherein the nanoantenna pattern is formed to have an array of one or more nanoantennas which are arranged at regular intervals; and
a pharmaceutically active ingredient impregnated in the porous micro-container of the structure;
a biosensor located on an outer surface of the drug delivery system and configured to detect bioinformation of the inside of a living body;
a transmission module configured to receive the bioinformation from the biosensor and wirelessly transmit the bioinformation to an external controller through the nanoantenna pattern formed on an outer surface of the drug delivery system;
a receiving module configured to wirelessly receive a drug releasing signal corresponding to the bioinformation from the external controller through the nanoantenna pattern formed on the outer surface of the drug delivery system;
an external controller configured to wirelessly receive the bioinformation from the transmission module and wirelessly transmit the drug releasing signal corresponding to the bioinformation to the receiving module; and
a power supply configured to supply power to the transmission module for the wireless transmission.

17. The drug therapy device of claim 16, wherein the power supply is a microchip-type cell or a biofuel cell attached to the outer surface of the drug delivery system, or obtains energy from the outside of the living body through electromagnetic waves.

18. A thermotherapy device using a thermotherapy complex, the thermotherapy device comprising:
a thermotherapy complex that comprises:
a structure which includes
a porous micro-container, and
a nanoantenna pattern formed on an outer surface of the porous micro-container, wherein the nanoantenna pattern is formed to have an array of one or more nanoantennas which are arranged at regular intervals; and
nanowires impregnated in a porous micro-container of the structure;
a biosensor located on an outer surface of the thermotherapy complex and configured to detect bioinformation of the inside of a living body;
a transmission module configured to receive the bioinformation from the biosensor and wirelessly transmit the bioinformation to an external controller through a nanoantenna pattern formed on the outer surface of the thermotherapy complex;
a receiving module configured to wirelessly receive a nanowire releasing signal corresponding to the bioinformation from the external controller through the nanoantenna pattern formed on the outer surface of the thermotherapy complex;

an external controller configured to wirelessly receive the bioinformation from the transmission module and wirelessly transmit the nanowire releasing signal corresponding to the bioinformation to the receiving module; and a power supply configured to supply power to the transmission module for the wireless transmission.

19. The thermotherapy device of claim 18, wherein the power supply is a microchip-type cell or a biofuel cell attached to the outer surface of the thermotherapy complex, or obtains energy from the outside of the living body through electromagnetic waves.

* * * * *